United States Patent
Böse et al.

(10) Patent No.: US 11,796,542 B2
(45) Date of Patent: Oct. 24, 2023

(54) RAPID TEST FOR THE DETECTING PATHOGENS AND CELLS AND METHOD

(71) Applicant: Zendia GmbH, Sendenhorst (DE)

(72) Inventors: Guido Böse, Sendenhorst (DE); Markus Ganter, Heidelberg (DE); Taleieh Rajabi, Karlsruhe (DE); Andreas Guber, Karlsruhe (DE); Ralf Ahrens, Karlsruhe (DE)

(73) Assignee: Zendia GmbH, Sendenhorst (DE)

( * ) Notice: Subject to any disclaimer, the term of this patent is extended or adjusted under 35 U.S.C. 154(b) by 1182 days.

(21) Appl. No.: 16/314,324

(22) PCT Filed: Jun. 30, 2017

(86) PCT No.: PCT/EP2017/066327
§ 371 (c)(1),
(2) Date: Dec. 28, 2018

(87) PCT Pub. No.: WO2018/002327
PCT Pub. Date: Jan. 4, 2018

(65) Prior Publication Data
US 2020/0124602 A1    Apr. 23, 2020

(30) Foreign Application Priority Data
Jun. 30, 2016  (DE) ............ 10 2016 112 024.3

(51) Int. Cl.
*G01N 33/543*    (2006.01)
*G01N 33/569*    (2006.01)

(52) U.S. Cl.
CPC ..... *G01N 33/569* (2013.01); *G01N 33/54306* (2013.01); *G01N 2333/005* (2013.01); *G01N 2333/195* (2013.01); *G01N 2333/4353* (2013.01); *G01N 2333/445* (2013.01)

(58) Field of Classification Search
None
See application file for complete search history.

(56) References Cited

U.S. PATENT DOCUMENTS

| | | | |
|---|---|---|---|
| 6,636,623 B2 | 10/2003 | Nelson et al. | |
| 8,962,260 B2* | 2/2015 | Sambursky | G01N 33/54346 436/514 |
| 9,957,554 B1* | 5/2018 | Wu | C12Q 1/6837 |
| 2006/0257993 A1 | 11/2006 | McDevitt et al. | |
| 2007/0015179 A1* | 1/2007 | Klapperich | B01J 20/28042 977/924 |
| 2010/0203521 A1* | 8/2010 | Klapperich | C01B 32/15 435/6.13 |
| 2010/0279309 A1* | 11/2010 | Sui | G01N 27/44791 435/7.1 |
| 2010/0297611 A1 | 11/2010 | Sambursky et al. | |
| 2012/0258469 A1 | 10/2012 | Babu et al. | |
| 2014/0073027 A1* | 3/2014 | Dholakia | G01N 21/05 435/173.6 |
| 2016/0124206 A1 | 5/2016 | Böse et al. | |

FOREIGN PATENT DOCUMENTS

| | | |
|---|---|---|
| CN | 1653480 A | 8/2005 |
| CN | 105388288 A | 3/2016 |
| CN | 105717310 A | 6/2016 |
| DE | 102007017051 A1 | 10/2008 |
| EP | 2746750 A1 | 6/2014 |

OTHER PUBLICATIONS

Trainito et al., Monitoring the permeabilization of a single cell in a microfluidic device, through the estimation of its dielectric properties based on combined dielectrophoresis and electrorotation in situ experiments, Electrophoresis, 2015, 36, pp. 1115-1122. (Year: 2015).*
Cassiday Laura, Getting the inside story on a single cell, Analytical Chemistry, Mar. 1, 2009, p. 1727. (Year: 2009).*
Search Report for German Application No. 10 2016 112 024.3 dated Apr. 27, 2017, with its English summary, English portions only.
Riglar et al., Spatial association with PTEX complexes defines regions for effector export into Plasmodium falciparum-infected erythrocytes, Nature Communications vol. 4, Article No. 1415 (2013).
Kong et al., Enhancing malaria diagnosis through microfluidic cell enrichment and magnetic resonance relaxometry detection, Scientific Reports vol. 5, Article No. 11425 (2015).
Fronczek et al., Paper microfluidic extraction and direct smartphone-based identification of pathogenic nucleic acids from field and clinical samples, RSC Advances 4(22):11103, Feb. 2014.
Di Carlo et al., Reagentless mechanical cell lysis by nanoscale barbs in microchannels for sample preparation, Lab Chip. Nov. 2003;3(4):287-91.
Comina et al., Towards autonomous lab-on-a-chip devices for cell phone biosensing, Biosens Bioelectron. Mar. 15, 2016;77:1153-67.
Partial International Search Report for PCT Application No. PCT/EP2017/066327 dated Oct. 6, 2017, with its English summary, 21 pages.
International Preliminary Report on Patentability for No. PCT Application PCT/EP2017/066327 dated Jan. 10, 2019, with its English translation, 26 pages.
First Office Action for Chinese Application No. 201780040901.5 dated Sep. 27, 2021, with its English translation, 11 pages, English portions only.

(Continued)

*Primary Examiner* — Gary Counts
(74) *Attorney, Agent, or Firm* — Rudy J. Ng; Bret E. Field; Bozicevic, Field & Francis LLP

(57) ABSTRACT

Provided is a test system including at least the following: permeabilising means and/or lysis of at least one pathogen and/or at least one cell, means for capturing and/or making parts of the pathogens and/or cells, means for localising, immobilising and/or enriching at least one component of a pathogen and/or a cell, means for image processing preferably including an optical magnifying unit, enabling an optical reading out of at least one means for localising, immobilising and/or enriching can be carried out.

5 Claims, 7 Drawing Sheets

(56) References Cited

OTHER PUBLICATIONS

Second Office Action for Chinese Application No. 201780040901.5 dated May 20, 2022, with its English translation, 10 pages, English portions only.
Office Action for Chinese Application No. 201780040901.5 dated Jan. 11, 2023, with its English summary, 12 pages, English portions only.
Search Report for European Application No. 17737240.6-1118 dated Feb. 2, 2023, 14 pages.
Office Action for Indian Application No. 201917003650 dated Nov. 3, 2022, with its English summary, 11 pages.

\* cited by examiner

Figur 1a:
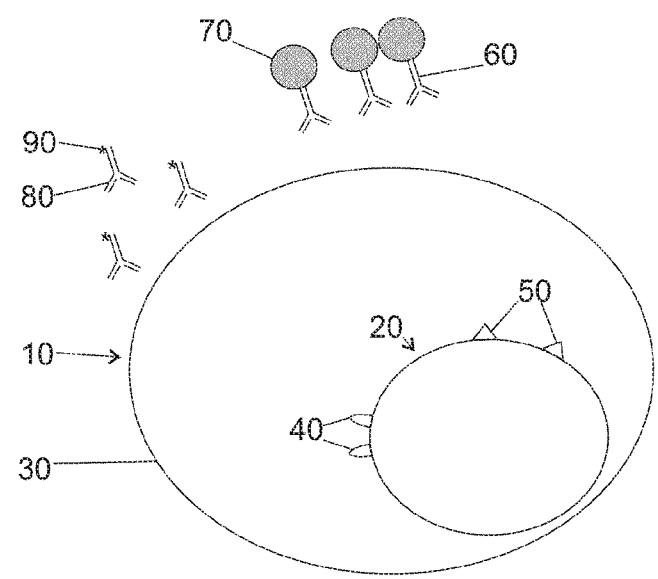

Figur 1b:
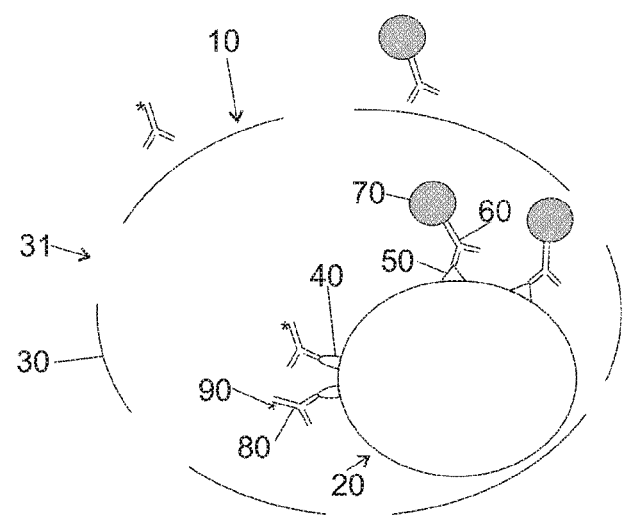

Figur 2a:
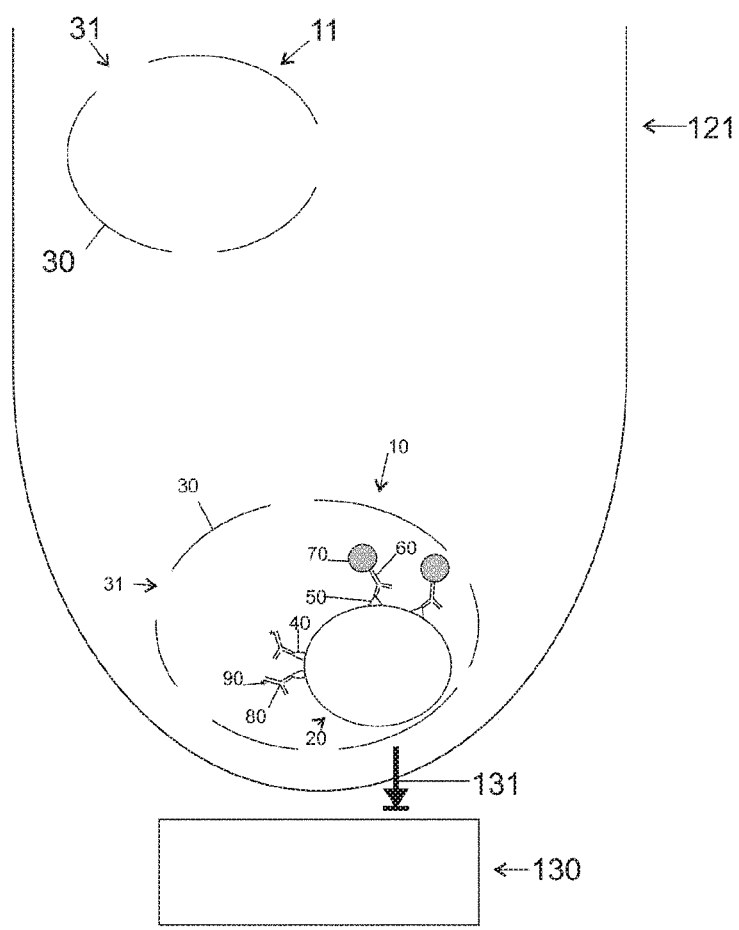

Figur 2b:
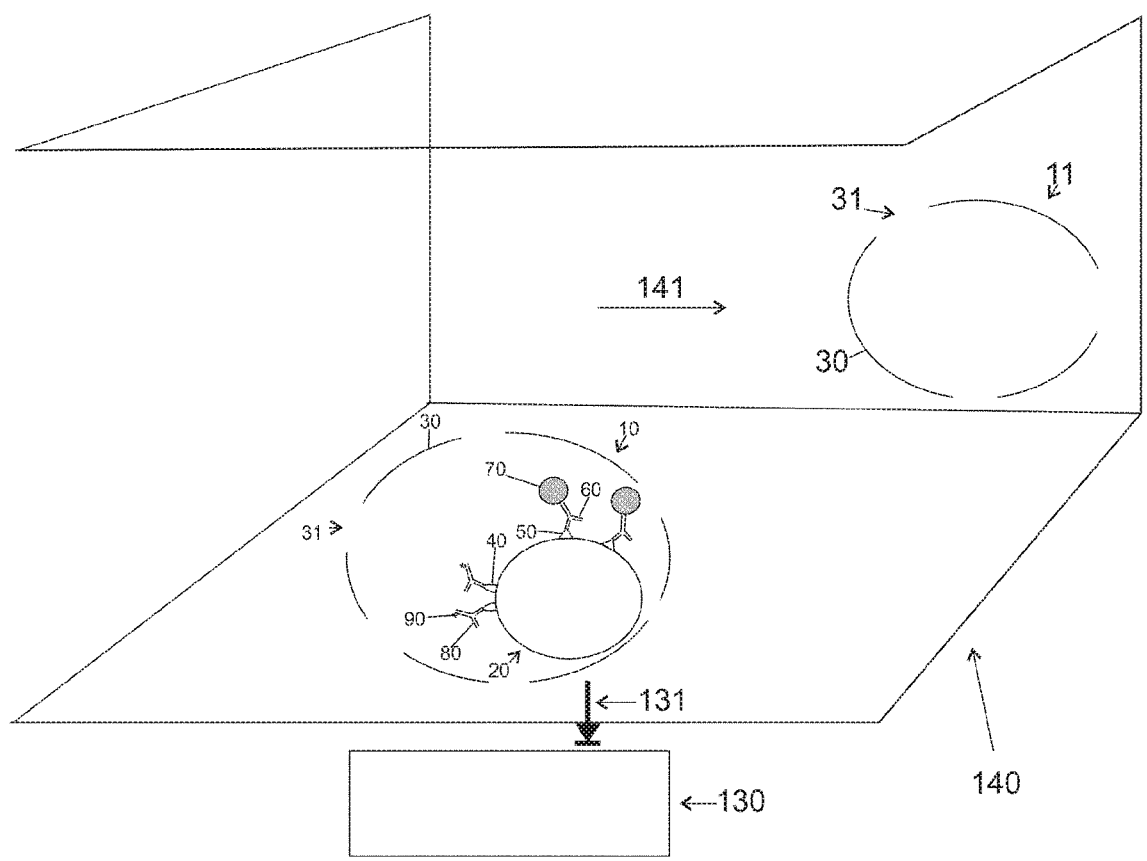

Figur 2c:
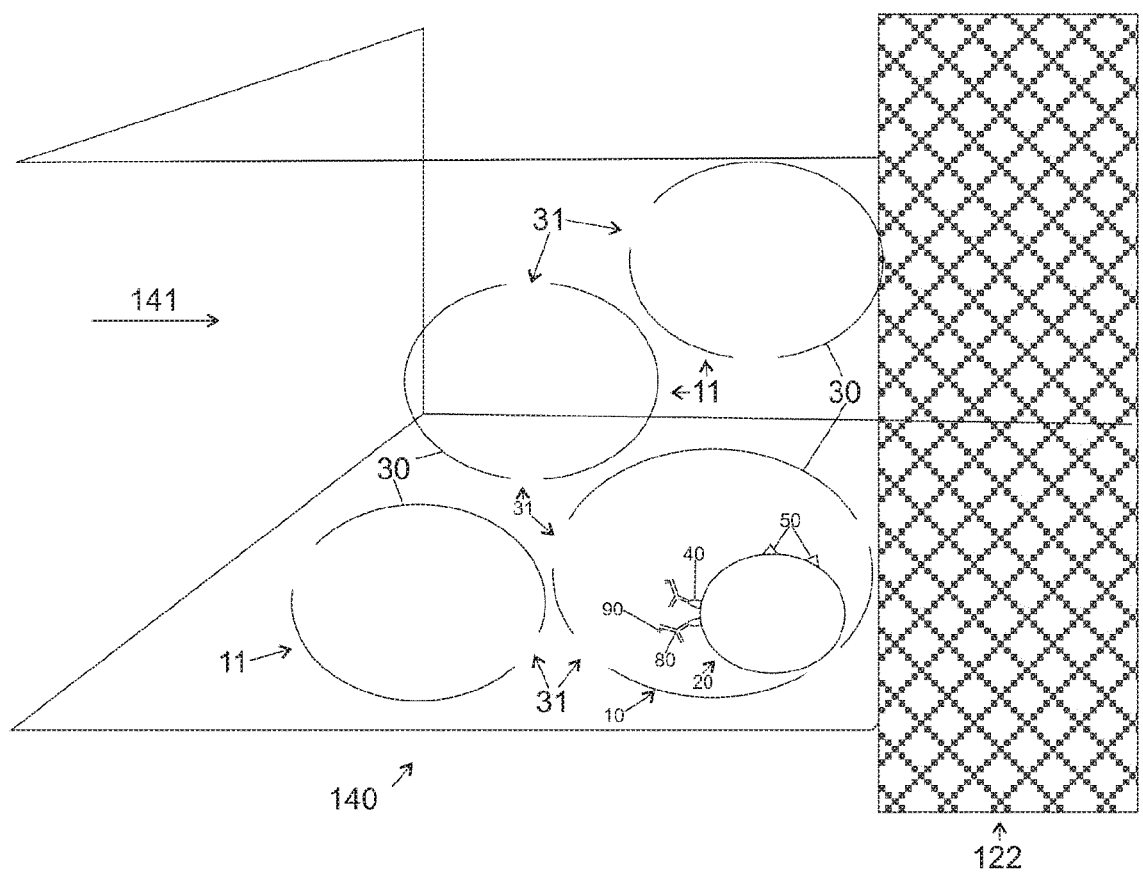

Figur 3:
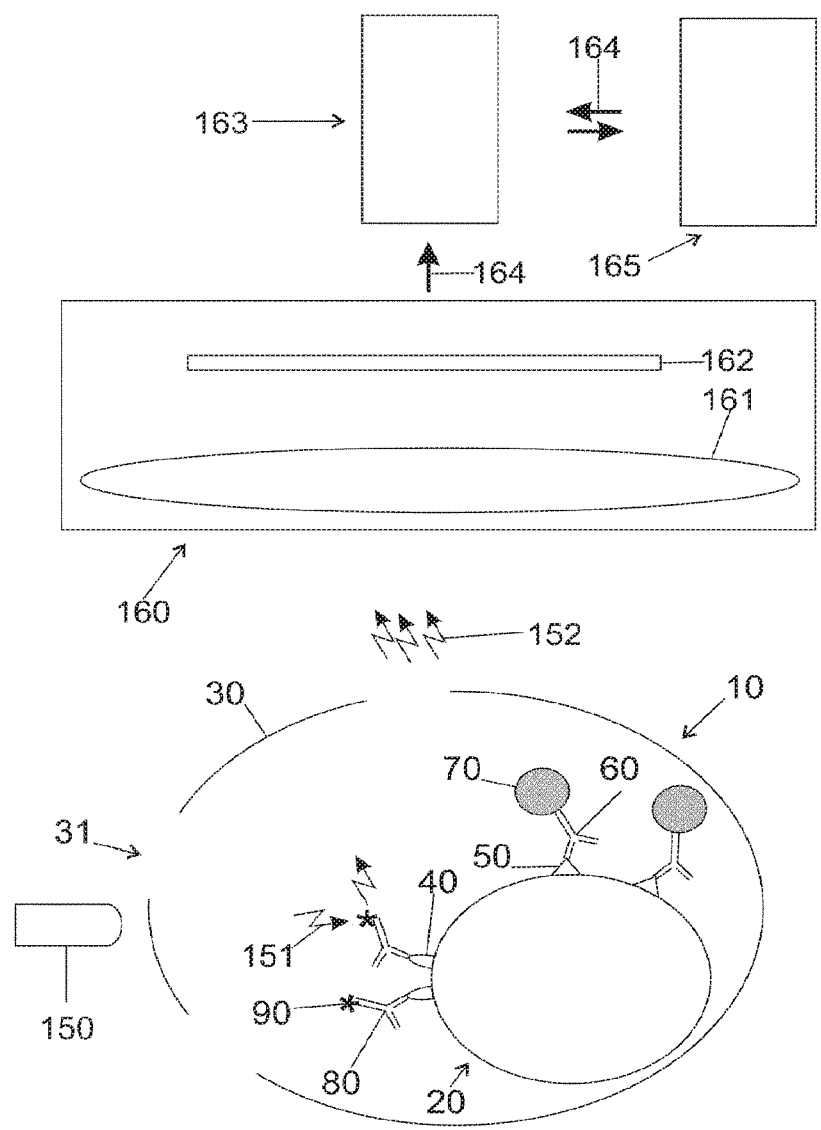

Figur 4:
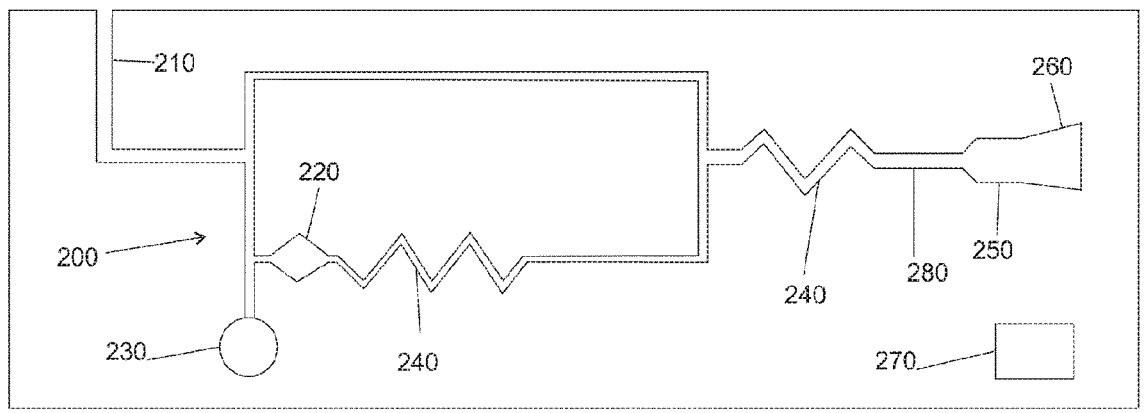

RAPID TEST FOR THE DETECTING PATHOGENS AND CELLS AND METHOD

FIELD OF THE INVENTION

The present invention relates to a test system for diagnosing diseases, to a test method for diagnosing diseases, and to a use of a test system and/or a test method for diagnosing diseases.

Test systems for diagnosing diseases are known in the prior art. For example, a number of analytical procedures and methods are used to trigger antibody reactions, so-called immune responses, which are used to determine (bio)markers and many other substances/analytes. Furthermore, microscopy-based methods are described in the field of diagnostics.

BACKGROUND OF THE INVENTION

Patient-centered or point-of-care (PoC) testing methods are diagnostic examinations that are carried out within a short time in situ, directly on the individual patient/subject, rather than in a central laboratory. PoC test systems are available for few parameters, such as immunochromatographic test grips which, by way of antibody binding, detect a soluble biomolecule, such as a hormone or a protein in the blood, urine or saliva using a color reaction. Known PoC test strips are, for example, pregnancy tests or blood coagulation tests, which are offered with or without measuring equipment. Moreover, associated rapid test methods are known, such as the lateral flow test (LFT), flow through test (FTT), agglutination test (AT) or solid phase test (SPT). All of these methods are used to detect analytes quickly and are suitable for visual evaluation in the PoC field. A robust and rapid diagnosis is required in the PoC field, which meets the special needs of emergency medicine, for example, without necessitating high mobility and/or connectivity to medical treatment specialists.

The disadvantage, however, is that no PoC tests exist for a large number of diseases, some of which are life-threatening and which are the subject of pathogen or cell diagnosis. These include severe bacterial infections, which may lead to sepsis, viral diseases such as influenza or diarrhea pathogens, diseases such as malaria, cholera and tuberculosis, or tests for quantifying certain blood cells, such as lymphocytes, in cancer patients. A complex examination, both in terms of equipment and staff, in a diagnostic laboratory is inevitable in the case of pathogen and cell examinations, which is accordingly time-consuming and cost-intensive, and moreover delays the start of an individually tailored treatment or therapy. In the case of malaria in particular, the standard method for diagnosis in the prior art is based on microscopy. A small amount of blood is sampled, of which a smear or a specimen is prepared in the form of a thick drop and stained with Giemsa stain. After fixation and drying of the specimen, the parasite can be identified under the microscope in the red blood cells (erythrocytes) and differentiated by the skilled practitioner. This method not only requires a trained person conducting it, but also a laboratory environment and an expensive microscope. Most regions prone to malaria do not have a laboratory equipped this way in the first place. Available molecular biology tests are also expensive and likewise require in-depth user expertise. Likewise, lateral flow rapid tests (supra) are known, which are able to detect parasite-specific antigens, but not the parasite per se or infected cells, and which consequently do not allow a pathogen or cell diagnosis. A robust and rapid diagnosis for quickly detecting pathogens at the site of sampling is also needed in the field of food and drinking water analysis to establish the source of an infection, initiate an appropriate treatment of affected patients, and prevent further people from becoming infected.

However, for a large number of pathogens no rapid tests exist at the site of the analysis, making complex laboratory examinations necessary. These include, for example, *Salmonella, Legionella,* enterohemorrhagic *E. coli* (EHEC), *Campylobacter coli* and *Campylobacter jejuni, Listeria monocytogenes, Mycobacterium avium* subsp. paratuberculosis or influenza viruses. In particular, the variability of the surface antigens presents a problem for any analytical detection that is based on identifying pathogens by way of the surface antigens thereof. These include immunoassays, for example, for the pathogens in rapid tests, such as the lateral flow test (LFT), flow through test (FTT), agglutination test (AT) or solid phase test (SPT). As a result, systems that analyze the pathogens and cells independently from surface antigens and can be utilized as PoC and/or rapid tests are of particular interest. Detection methods using DNA or RNA analytics, such as by way of PCR or a cultivation of the pathogens, are complex, both in terms of equipment and time, and expensive. A great need therefore exists for the development of a test system that includes an analysis independent of surface antigens, in the form of a PoC and/or rapid test, and allows a complex diagnosis. The complex diagnosis is to enable, in particular, diagnosing pathogens and cells from body fluids or foods and/or drinking water.

SUMMARY OF THE INVENTION

It is therefore the object of the present patent application to provide a test system and a test method, and a use of the test system and/or the test method, which at least partially overcome the aforementioned disadvantages. In particular, it is the object of the present invention to cost-effectively detect a wide variety of pathogens and/or cells in a short time, in particular independently from laboratory equipment.

To achieve this object, a test system for diagnosing diseases, a test method for diagnosing diseases, and a use of the test system and/or test method as described herein are proposed, which hereafter are of great importance. All technical features that are disclosed with respect to the test system according to the invention for diagnosing diseases also apply to the test method according to the invention for diagnosing diseases and to the use of the test system and/or the test method, and vice versa, so that mutual reference is made, or can be made, in this regard in each case. Advantageous embodiments of the invention are disclosed in the dependent claims.

The invention relates to a test system for diagnosing diseases. The test system comprises at least one means for permeabilizing and/or lysing at least one pathogen and/or at least one cell, and/or a means for binding and/or labeling parts of the pathogens and/or cells, and/or a means for localizing, immobilizing and/or enriching at least one component of a pathogen and/or a cell, and/or a means for image processing, whereby an optical read-out of at least one means for localization, immobilization and/or enrichment can be carried out. Preferably, the read-out can take place by way of a provided optical magnifying unit. As an alternative or in addition, it is conceivable that the read-out can take place by way of a mobile processor unit. By permeabilizing and/or lysing a pathogen and/or a cell in accordance with the invention, it is possible to ensure that agents for binding and/or labeling, and preferably fluorescent labeling, have access to structures which would not be accessible without these means due to compartmentalizing structures, such as a lipid membrane or a cell wall. In combination with a means for localization, immobilization and/or enrichment, it is thus possible to situate parts of the pathogens and/or cells from a liquid sample. In this way, a means for image processing can be used to optically read out the tag, and sufficient intensity and a sufficient contrast effect can be achieved for one or more images, which can be read out by way of the optical magnifying unit the and image processing device in the mobile processor unit, so that effective image processing can take place, and the sought pathogens and cells can thus be detected using imaging. With specific immunostaining and/or specific DNA staining, infected cells show up in the contrast as stained and/or fluorescent spots and/or areas against a lesser colored and/or lesser fluorescent background, while non-infected cells may be invisible and/or may remain only slightly visible. In the presence of an illumination device, and in particular an excitation illumination device, the image evaluation of the color contrasts of stained and/or fluorescent cells can take place against a lesser colored and/or fluorescent background. By determining lighter spots and/or areas, it is possible to ascertain the number of infected cells per volume of the sample by counting and calculation. Within the scope of the present invention, an optical magnifying unit may represent a unit that can contain at least one objective and/or a system of one or more objectives and/or lenses, similarly to a microscope, which can have sufficient magnification power. Such magnification can be achieved, for example, in conjunction with a microscope. When such a microscope is used, it is also possible, as an alternative, to transmit image data directly to the processor unit.

Within the scope of the invention, magnification powers of the optical magnifying unit in the presence of the image processing device of preferably approximately 2.5 times to approximately 5 times, and preferably approximately 10 times to approximately 1000 times, are conceivable. The resolution may be approximately 5 µm, preferably approximately 0.1 µm to approximately 2 µm, and in particular approximately less than 0.5 µm. In this way, sufficient magnification of cells and/or pathogens can be achieved. The magnification factor can be fixed or variable. To set the focal plane and/or the magnification, a variable lens, such as a liquid lens, for example from Optotune Switzerland AG or Vario-Optics AG, can be used. The optical magnifying unit or image processing device can preferably include one or more arbitrary light sources, such as a white light and/or fluorescent illumination unit. The fluorescent illumination can be used as the excitation light for fluorescent dyes.

Furthermore, according to the invention an image processing device for the mobile processor unit may be provided, in particular in the form of a camera. The image processing device can be used to detect image data of an optical magnifying unit. Within the scope of the present invention, a mobile processor unit may represent a unit that is provided, for example, by a mobile phone having a processor function (smart phone) and/or by a laptop and/or tablet processor (tablet, tablet computer). The mobile processor unit can, essentially, include a central unit and/or a processor, which is able to carry out the computing and process steps required for image processing.

The image processing device can furthermore include an analysis mode, wherein total gray scales, color values and/or color contracts, and preferably fluorescent signals, can be detected in part of an image. The detection may be qualitative and/or quantitative. Within the scope of a simple quantitative evaluation, information as to whether areas exceed an established critical intensity value can be provided. This critical value is empirically established for the test system and is used, for example, for differentiation from the background signal of the labeling ligand of specifically bound labeling ligands which is still present in the solution in the case of immunofluorescence. The image processing quality may be enhanced by consecutively examining individual parts of an image of a larger field. This may be done by pure selection in the image processing operation. As an alternative or in addition, the image processing quality can likewise be achieved by an optical magnification of a respective part of an image, wherein, for example, a delimited object having an intensity that exceeds a critical value can be defined as a pathogen.

Furthermore, it is conceivable to carry out a quality analysis within the scope of the image evaluation. This allows the standard deviation of the results in multiple parts of the image to be calculated. As an alternative or in addition, it can also be ascertained how close a calculated value is to a critical value. The poor quality of the measurement can be inferred from the fact that the calculated value is in close proximity to the critical value or in the case of a large standard deviation. Moreover, a new test may also be prompted. To use the present invention, likewise a program can be carried out a processor unit, for example in the form an app on a smart phone, which has at least one of the following basic functions: reading in image data, image processing, quantitative and/or qualitative output of an image processing and/or analysis result. The program may additionally include a quality analysis with respect to the quality of the analysis of a sample. It is furthermore possible to link the program to further information, in particular internal or external databases on clinical pictures, addresses of medical services, transmission of pathogen images to medical treatment specialists and the like.

It is likewise conceivable for the test system to comprise means for localization, immobilization and/or enrichment and elements for receiving a sample fluid. In particular, it is advantageous when the sample fluid stems from a body fluid and/or a food sample and/or drinking water. A body fluid can preferably be blood, whole blood, urine, saliva, synovial fluid, cerebrospinal fluid, plasma and/or serum and/or lacrimal fluid, sweat, lymph and/or intercellular fluid. For example, a sample of a body fluid of a patient may be treated with arbitrary chemicals, reagents, in particular stains and dyes, in particular fluorescent dyes, if necessary along with customary auxiliary substances and additives, such as anti-coagulants, protease inhibitors, stabilizers and/or enzyme inhibitors. Patients shall be understood to mean any subject, regardless of symptoms and/or disease, more particularly humans and animals, and in particular mammals. Such body fluids contain analytes, and in particular cells that can contain infected cells and/or pathogens per se. Pathogens are, in particular, bacteria, fungi, viruses and/or parasites. A sample fluid of a food sample can comprise any arbitrary dilution, solution, an extract and/or a swab of a food. A sample fluid of drinking water can furthermore comprise an unaltered and/or concentrated and/or diluted sample and/or a liquid receiving portion of a filtration residue.

Furthermore, it may also be advantageous when the test system comprises means for permeabilization, wherein advantageously it can be achieved that ligands have access to at least one biomolecule and/or to at least one structure of a pathogen and/or to at least one cell. In particular, it is conceivable that the structure and/or the cell can have an opening measuring between approximately 1 nm and approximately 12 µm. It is also possible to generate complete lysis of the cell. Permeabilizing and/or lysing pathogens and/or cells can be a process for generating a temporary and/or permanent permeability of outer and/or inner cell membranes, cell walls, murein envelopes, viral envelopes and/or lipid membranes and/or other compartmentalizing structures, so as to enable antibodies, labeled antibodies, ligands and/or magnetic particles loaded with ligands to have access to inner structures, antigens and/or biomolecules of the pathogens and/or cells. A means for permeabilizing and/or lysing pathogens and/or cells may comprise a unit and/or a substance that provides accessibility to biomolecules and/or structures of the pathogens and/or cells, which in living pathogens and/or cells, for example, are generally partitioned off by a lipid membrane, a cell wall, a viral envelope and/or another cell-enveloping layer, and are thus not accessible for immunoanalysis, for example. Such a means can provide pores in a membrane, for example through pore proteins, and/or destabilize the membrane, through cholesterol withdrawal, and generate openings in the membrane, and/or cause openings in the cell membrane, through osmotic effects such as swelling and bursting of the cells, and/or generate openings, through electrical and/or mechanical pulses. A means can furthermore also comprise all other means that are able to provide one or more openings in a cell membrane, cell wall, viral envelope or lipid membranes and/or enable penetration of the same, for example through means employed similar to transfection, such as fused and/or imported vesicles, magnetic particles and/or penetrating nanoparticles. These means may be substances for permeabilization and/or lysis, such as saponins, for example for the lysis of erythrocytes, bacteria, fungal cells and/or other eukaryotic cells, digitonin for temporarily permeabilizing eykaryotic cells, for example, porins for permeabilizing lipid membranes, for example, streptolysin O and equinatoxin II, ammonium chloride for lysing erythrocytes, for example, detergents such as deoxycholates, triton X100, NP-40 and/or other substances such as acetone and/or ethanol for destabilizing the cell membrane, ethylenediaminetetraacetic acid for permeabilizing the outer membrane of gram negative bacteria, lysozyme and/or autolysine for lysing the peptidoglycan cell wall of gram positive bacteria, lactoferrin, defensin and cathelicidin for gram-negative bacteria and other substances, but also an electric field which, similarly to electroporation, is able to temporarily and/or permanently render the cell membrane permeable, and/or mechanical and/or other action that results in permeabilization and/or lysis, and provide enhanced access of ligands to biomolecules of the pathogens and/or cells. These means can be combined with fixation substances such as paraformaldehyde, glutaraldehyde, acetone, methanol and ethanol. The sizes of the generated openings may be in the range of approximately 1 nm to approximately 12 µm and result in temporary permeabilization for a few milliseconds to permanent lysis of the cells. Likewise conceivable are means that can be used to receive ligands and/or magnetic particles without forming openings, such as means that can also be used with transfection, such as vesicles, magnetic particles, penetrating particles, and import-triggering substances. Moreover, these may be means that result in a release of biological structures and/or molecules and/or other parts of the pathogens and/or cells, which would remain inside the cells and/or pathogens without these means, and would thus be shielded against identification by the immune system. This may comprise lysis and/or another destruction of the pathogens and/or cells and/or the induced release and/or liberation of biological structures and/or molecules through export and/or through pores and/or openings.

It may likewise be advantageous within the scope of the invention if means for localizing, immobilizing and/or enriching at least one component of pathogens and/or cells can be used for the test system. At least one component of pathogens and/or cells may be enrichable. In one embodiment, the means for localization, immobilization and/or enrichment can be a reaction vessel, such as an Eppendorf reaction vessel, and/or a filtration column. In this, a sample and/or means for permeabilization and/or means for binding and/or means for labeling can be miscible with one another and, for example, be immobilized by way of a magnet and detected by way of a means for image processing, such as a fluorescence spectrometer and/or an imaging fluorescence microscope. In addition or as an alternative, it is likewise conceivable that the means for localization, immobilization and/or enrichment can include a microfluidic structure for dissolving and/or mixing substances. Such a means for localization, immobilization and/or enrichment can preferably be a test strip including a microfluidic structure. Such a test strip is preferably made of one or more transparent materials, such as a planar plastic material and/or glass, which may be able to receive a body fluid and/or another liquid sample. In a preferred embodiment, a sample may pass through the test strip, in particular by way of at least one incorporated and/or applied channel and/or microchannel, and in particular having a rectangular, trapezoidal and/or arc-shaped cross-section. The channel can be a capillary and/or allow laminar and/or non-laminar flow under the action of gravity and/or a capillary force and/or pumping forces and/or other forces.

The test strip can preferably include the execution of the detection method of pathogens and/or cells, including receiving a sample, adding and mixing with one or more means for permeabilization, adding and mixing with one or more means for binding and/or for labeling structures of the pathogens, cells and/or the components thereof, incubating the sample, subsequently localizing, immobilizing and/or enriching the pathogens and/or cells and/or the components thereof in a detection area. For small volumes of a few microliters, the test strip may furthermore preferably provide a device for maintaining a flow, and may provide connections to external pumping systems for larger volumes of up to several liters. The sample receptacle, in the simplest case, can comprise a reservoir to which a defined volume, in particular of a few microliters, of a sample can be placed, for example using a micropipette. In the case of volumes of several liters, these may be added via a connection by an external system. The sample receptacle may be provided with (dried) chemicals, such as EDTA, heparin for anticoagulation and/or dyes for histological cell staining, which may be dissolved by the added sample. In the case of capillary whole blood from the finger pad, receiving can preferably take place by way of a capillary having a defined volume and a level indicator. The whole blood can preferably be suctioned into the same until completely full, thus providing a defined volume. If the capillary is located, for example, in a cover matching the test strip, the defined blood volume can thereafter by applied therein by placing the cover onto the test strip. In this embodiment, the cover can preferably include structures that irreversibly latchingly engage when placed on the test strip. A further embodiment can include a microfluidic structure having a defined volume associated with the test strip, into which the whole blood is suctioned and which, for example by a displacement of the capillary and/or by way of microvalves and/or other devices, can make contact with the further microfluidic system after the volume has been defined so that the whole blood can be applied therein. The application of the means for permeabilization and/or lysis and of the means for binding and/or for labeling specific structures can take place by way of a solution of lyophilized substances through the sample flowing past. A distinction must be made here between the leading volume of the sample behind the dye front and the trailing volume of the sample. In this procedure, the leading volume in the test strip can comprise more dissolved substance than the trailing volume. For this reason, the test strip can preferably include at least one mixer structure, which can mix the dissolved substances with the sample. In the case of a microfluidic structure, this may be a mixing chamber with and/or without external mechanical action, a zigzag structure and/or another device for mixing. A further embodiment can include splitting the microfluidic sample flow into at least two channels, wherein the lyophilized substances can be admixed to a sample portion in a first channel and, in the second channel, a sample portion can be conducted past the same. Thereafter, at least some of the channels can be combined again, and the two sample portions can be mixed with one another in a mixer structure. The flow rates can preferably be determined by the channel dimensions. Using such an embodiment, it can be achieved that the trailing sample volume from the second channel can also still be mixed with sample volume containing substances from the first channel. At the same time, immunofluorescence staining using a labeling ligand can be carried out. The infected cells and/or pathogens can be stained by adding a labeling ligand to the now empty sample port, by dissolving lyophilized substances and/or from a blister reservoir, which can be opened by way of mechanical action, and the content of which can be partially or completely discharged into the test strip. The test strip may preferably provide a device for maintaining the flow for small volumes of a few microliters, and it may provide connections to external pumping systems for larger volumes of up to several liters. In a further embodiment, the device for maintaining the microfluidic flow can preferably comprise a capillary pump provided downstream from the detection area, which draws liquid into a waste compartment subdivided by microstructures using capillary forces. In a further embodiment, a material exerting a suction force, such as a non-woven filter and/or an absorbent non-woven, can be integrated into the test strip so as to have contact with the microfluidic channel at least temporarily, and preferably can draw liquid through the test strip. In a further embodiment, a micropump can preferably be integrated into the test strip, which can control the flow. This may be a punch that pushes liquid out of the blister into the microfluidic channel, a suction device, which suctions liquid from the channel using negative pressure, and/or another device, such as the mp6 micropump from Bartels Mikrotechnik GmbH. Moreover, a bar code can be printed onto a test strip and/or an RFID element can be integrated therein, which can contain customary information regarding the test strip, for example the type of test (for example, diagnosis for malaria pathogens, legionella and/or sepsis) and/or the expiration date of the test strip, and the like.

Furthermore, the test system can comprise means for localization, immobilization and/or enrichment, which can include a microfluidic structure for incubating a sample fluid with a capture ligand and/or labeling ligand, and at least one detection area. At least one component of at least one labeled pathogen and/or of at least one labeled cell can be receivable on the means for localization, immobilization and/or enrichment. The means for localization, immobilization and/or enrichment can allow the specific labeling of pathogens, cells and/or the components thereof, preferably with a dye and/or a fluorescent dye, fluorescent and/or non-fluorescent nanoparticle and the like, and/or combined with a ligand, such as an antibody, by adding a labeling ligand and/or preferably the solution of lyophilized labeling ligands. It is particularly advantageous when, according to the invention, no additional washing step may be needed. Depending on the analyte and/or test execution, the stain can preferably be a simple histological stain of the cell plasma, of a lipid membrane, of a cell wall and/or the DNA and/or an immunochemical stain, such as a fluorescent stain. The background signal of the specific tag due to the staining solution remaining in the channel, for example, may be irrelevant during the measurement since the staining solution can preferably have a low concentration. As soon as the staining liquid is distributed in the channel and/or has flown therethrough, one or more unbound labeling ligands may be present distributed in the channel, which can bind to markers of the pathogens and/or cells made accessible by permeabilization. The concentration of the labeling ligands in the staining liquid is preferably selected in such a way that labeling ligands can be enriched on the infected cells, pathogens and/or the components thereof, as compared to the free labeling ligands present in the liquid. In this way, pathogens, cells, infected cells and/or the components thereof can preferably appear in the contrast as light stained/fluorescent spots and/or areas against a stained/fluorescent background, while other liquid components, such as non-infected cells, may remain invisible and/or only slightly visible. The sample may be incubated, for example, using one embodiment of the test strip which can include an incubation structure. This can be a zigzag structure, for example, through which the flow can take place in time periods from a few seconds to several minutes, both mixing the sample and allowing incubation. In a further embodiment, substances for permeabilizing and/or lysing the pathogens and/or cells may be charged in lyophilized form and, as described, be dissolved by a portion of the sample volume, mixed into the sample and incubated. If the pathogens and/or cells are then non-specifically or specifically retained, immobilized and/or captured in the microfluidic structure, it is also possible to sequentially add the labeling ligand for labeling the sought structures. In one embodiment, a liquid for washing and/or a capture ligand and/or a labeling ligand may be added externally. In another embodiment, the test strip may include a blister filled with liquid, which can be opened by the user and/or a device, such as a mechanical punch in the means for receiving the test strip, such as an optical reader. The liquid may reach the microfluidic channel and either already contain the ligands and/or may be dissolved from a charged, lyophilized form in the channel and subsequently flow around the pathogens and cells. Such a test strip can preferably include a detection area of the microfluidic channel, in which preferably fluorescent labeled pathogens, cells and/or the components thereof are immobilized and preferably can be enriched by being held back, while the remaining liquid can flow onward to a collection reservoir. The detection area can have an arbitrarily sized and arbitrarily configured design. However, an extent that can be received in one or more areas of images of the magnifying lens can be preferred. In a further embodiment of the test strip according to the invention, bars and/or markings can be printed in and/or next to the detection area, preferably orthogonal to the direction of flow. These may be used to visually delimit and/or subdivide the detection area for image processing and/or for determining the implemented pull-through speed of the test strip by an evaluation unit.

Furthermore, the test system can contain a means for localizing, immobilizing and/or enriching at least one microfluidic structure made of PET into which an aqueous liquid flows, preferably passively, as a result of the material properties of the PET, having no further coating. This microfluidic structure can be closed entirely and/or in part by a film, instead of by a rigid cover. The structure can be divided into one or more areas, which are initially closed, which is to say form a "dead end," whereby the liquid does not flow further through the same, and through which liquid can flow after opening, for example piercing of a film, via a ventilation opening located downstream therefrom. This can, in particular, form a subdivision into a sample receiving area, a mixing area and a detection area. Based on capillary forces, a defined sample volume of a liquid, such as whole blood from the finger pad, can be received in the sample receiving area. As soon as a first ventilation opening is reached, the inflow comes to a halt, and the user can read the fill level from a vision panel. Thereafter, or at least partially simultaneously, a mixing area can be provided, downstream from which a second ventilation hole can be provided, which is closed initially. If the film is opened over the same and pierced, for example, the sample flows into the mixing area in which the sample can preferably be mixed with lyophilized substances, such as an anticoagulant and/or a capture ligand, with or without magnetic beads, and/or one or more labeling ligands and/or stabilizers and/or a means for lysis and/or permeabilization. To intensify the mixing process, mixing structures, such as fishbone patterns in the channel, a direction-alternating external magnetic field, vibrations, sound or other mixing methods can be employed. The sample receiving area and the mixing area can also overlap or be identical. A detection area can be provided downstream, which provides a vision panel for imaging microscopic measurement. When a ventilation hole that is located downstream from the detection area and closed, for example, by a film is opened, the sample flows into the detection area. The pathogens can be localized and/or enriched and/or immobilized, preferably by an external magnetic field, therein and represented using imaging.

Furthermore, the test system can likewise include means for binding at least one capture ligand and/or at least one labeling ligand for labeling, and in particular staining. In particular, at least one antibody, one aptamer and/or one ligand may be included for this purpose, and/or a microparticle, nanoparticle or magnetic nanoparticle may be included, which can be coupled to an antibody, aptamer or ligand. Preferably, furthermore an at least magnetic nanoparticle, preferably a Turbobead and/or a metal core, can be couplable to at least one component of pathogens and/or cells by way of a coupled ligand. Preferably, a sandwich structure composed of at least one capture ligand and at least one labeling ligand can be generated. Means for binding and/or labeling can comprise one or more capture ligands and/or labeling ligands, which can preferably bind to antigens and/or biomolecules of entire, or of parts of, cells and/or pathogens. Ligands can preferably be antibodies, aptamers, peptides, protein ligands, microparticles, nanoparticles, magnetic beads, reactive substances, but also other ligands and/or a combination of those described, which can specifically bind to so-called markers such as antigens, biomolecules and/or other structures of the pathogens and/or cells and/or the components thereof. It may only be by way of a means for permeabilization that these ligands can come in contact with markers such as biomolecules, structures and/or antigens of the pathogens and/or cells, from which, in the absence of the means for permeabilization, these would be separated by a cell envelope, cell membrane, cell wall, viral envelope, lipid membrane and/or another compartmentalizing structure. Capture ligands can be used to immobilize the pathogens, cells and/or the components thereof so as to, preferably, achieve an enrichment across a detection area. In the case of magnetic particles, such as preferably magnetic microparticles, in particular Dynabeads or magnetic nanoparticles (MNPs), and in particular Turbobeads, but also other non-fluorescent and/or fluorescent MNPs, with or without bound antibodies, aptamers and/or ligands, this may involve the immobilization of bound pathogens, cells and/or the components thereof, preferably at the bottom and/or the top of a microchannel, across a detection area by way of a magnet. In the case of immunochemical staining, labeling ligands can be used, which can preferably bind to a second, independent binding site of pathogens, cells and/or the components thereof. These ligands can preferably be coupled with a fluorescent dye, fluorescent nanoparticles such as quantum dots and/or dye, magnetic particles and/or gold particles, so that, by these ligands binding to the cell surface, a sufficient signal, preferably a fluorescent signal, can be created and preferably rendered visible against the background, preferably by way of optical magnification, whereby individual depictable color values, gray scales and/or contrast can be created. The invention can thus likewise relate to a test system, wherein the analytes, cells, pathogens bound to the test strip are labeled by way of a labeling ligand, which is coupled to a dye, preferably a fluorescent dye, stain, nanoparticle, magnetic particle and/or gold particle, and can preferably be rendered accessible to image evaluation. Preferably, double identification in the sandwich system can take place on the one hand, for example, by a capture ligand made of specific antibodies on a magnetic particle and, on the other hand, by a labeling ligand, such as a fluorescent labeled antibody. This can allow unambiguous typing of the infected cells and/or pathogens and preclude false positives due to non-specific binding of other cells and/or due to non-specific staining of other cells. For example, infected cells (for example in the case of malaria) and/or pathogens (for example *Legionella, Salmonella,* streptococci and the like) can comprise appropriate markers, to which the ligands (capture ligands and labeling ligands) have access after permeabilization and which can be detected by the same. The method can enable the enrichment and unambiguous visual identification of cell types, such as malaria-infected erythrocytes, CD4+ cells and/or likewise infected cells in the diagnosis of HIV, likewise the identification and typing of bacteria, for example, in the diagnosis of sepsis, legionella, cholera, tuberculosis and the like. In addition, it is possible to use coupled enzymes as labeling ligands for an enzymatic detection reaction, whereby a color reaction and/or electrochemical reaction can be created, which is detectable. In one embodiment of the test strip, a filtration device comprising, for example, a filter material such as a "Vivid" Plasma Separation Membrane from Pall Corp., a microporous and/or nanoporous membrane having subcellular pore diameters and/or other structures having a straining function may be present. This may allow the liquid to pass through, but retain nonspecific pathogens and/or cells or the components thereof as a function of their size. This may be integrated on a channel end and/or laterally in a channel wall. The retained pathogens, cells, infected cells and/or the components thereof can be specifically labeled by one or more labeling ligands. When labeling ligands are used, such as of fluorescent labeled antibodies, aptamers and/or other ligands, specific staining of the sought structures of the pathogens, cells and/or the components thereof can take place. In one embodiment of the invention, the test strip can contain a filter for the nonspecific retention of all cells and/or pathogens, while the labeling of the sought pathogens can preferably take place by specific binding of fluorescent labeling ligands in immunofluorescent staining. If only the sought pathogens have DNA, as is the case with plasmodia compared to DNA-free erythrocytes, it is also possible to fluorescent stain the DNA, which may specifically label the plasmodia. For control purposes, membrane staining can be carried out at the same time to identify all cell contours by way of white light and/or using spectrally separated fluorescence detection. In one embodiment, magnetic particles can preferably be coupled to the ligands, which can specifically bind to the cellular structures, enabling magnetic capturing thereof and enrichment by the application of an external magnetic field. If a magnet is integrated in the detection area of the test strip and/or in the means for receiving the test strip, such as a read device, the magnetic force can thus preferably cause the magnetic particles in the test strip to be immobilized, such as at the bottom and/or at the top of a microfluidic channel. Commercial magnetic particles, which can typically be used for capturing cells via surface antigens by way of antibodies, aptamers and/or ligands, can in particular have a diameter of approximately 1 nm to approximately 12 µm. Thermo Fisher Scientific, for example, offers Dynabeads Myone magnetic microparticles having a diameter of 1 µm, or Dynebeads having a diameter of 2.8 µm, comprising different surface groups such as streptavidin, biotin and/or chemical coupling groups such as azide and/or amino groups for binding biomolecules, antibodies, aptamers and/or ligands.

These microparticles may be too large to penetrate through the generated openings in permeabilized pathogens and/or cells and/or to be received by other techniques. For example, this can be done only after the pathogens and/or cells have been lysed and fragmented, thereby providing access to the microparticles to structures on the inside. The pathogens and/or cells can preferably be permeabilized, yet the shape thereof given by the cytoskeleton can be preserved, and they can remain physiologically identifiable. Magnetic nanoparticles (MNPs) can have a diameter of approximately 5 nm to approximately 500 nm and thus penetrate through openings in permeabilized pathogens and/or cells. In another embodiment, non-fluorescent MNPs can be used together with coupled antibodies, aptamers and/or ligands so as to be able to specifically bind to antigens and/or structures after the sought pathogens and/or cells have been permeabilized. By way of magnetic force, the MNPs can be immobilized with the bound pathogens, cells and/or the components thereof in the detection area, for example to the channel top and/or the channel bottom. Preferably, a labeling ligand can generate a specific, detectable signal on the sought pathogens, cells and/or the components thereof. If fluorescent labeled antibodies, aptamers, nanoparticles and/or ligands are used, immunofluorescence may result in the sandwich design. As an alternative, the DNA of plasmodia can be stained by way of a fluorescent and/or non-fluorescent DNA stain. The MagVigen particles from Nvigen Inc. have diameters of 200 nm to 500 nm, for example, and the surfaces thereof include coupling groups and/or proteins. In this way, chemical coupling can be made possible for binding specific antibodies, aptamers and/or ligands, or else by way of proteins present on the MNPs, such as avidin and/or a secondary antibody. Ocean Nanotech Inc. offers various paramagnetic beads starting at a diameter of 50 nm, likewise including different surface groups, for example for antibody coupling. Turbobeads Llc. likewise offers magnetic nanoparticles, referred to as Turbobeads, including different surface groups such as streptavidin, biotin and/or chemical coupling groups such as azide and/or amino groups for binding biomolecules, antibodies, aptamers and/or ligands. Turbobeads can have diameters of approximately 30 nm, but preferably have three times stronger magnetic properties through the use of a metallic core instead of the ferrite core customarily used in MNPs. This allows for the magnetic separation to take place considerably faster and more efficiently than with customary MNPs. Magnetic nanoparticles that are also fluorescent can bind the target structures by way of coupled antibodies, aptamers and/or ligands and be used not only for magnetic capturing, but also for fluorescent labeling. The magnetic and fluorescent MyQuVigen particles from Nvigen, Inc., as well as the NanoScreenMag MNPs from Chemicell GmbH are likewise offered with different surface groups, for example for antibody coupling. This combination can have the advantage of a simple procedure of simultaneously immobilizing the labeled pathogens by way of a magnet and fluorescent labeling. However, since all magnetic, fluorescent nanoparticles can be captured, a fluorescent background can be created by individual, unbound particles, which must be reliably distinguished from MNPs bound to pathogens. The immobilization of the pathogens, cells and/or the components thereof can preferably be separated from the labeling process, which is to say that separate capture ligands and labeling ligands and used.

The object is furthermore achieved by a method for diagnosing diseases. The method according to the invention entails the same advantages as those that were described in detail with respect to the system according to the invention.

According to the invention, the test method for diagnosing diseases comprises at least one of the following steps: applying a sample fluid, in particular a liquid to the means for localization, immobilization and/or enrichment. In the case of a microfluidic structure, this may even allow the method to be used at the point of care, for example, by simply taking up a drop of capillary blood from the finger pad, by an untrained person and automatic processing of the sample in a closed means for localization, immobilization and/or enrichment, without requiring any further intervention by the user and/or laboratory equipment, for example for the precise addition of a substance, pathogen cultivation, centrifugation and the like.

As a further step, a means for permeabilization can be applied and/or released onto the means for localization, immobilization and/or enrichment, whereby it is ensured that ligands have access to structures of at least one pathogen and/or of at least one cell contained in the sample fluid. This can preferably take place by dissolving a substance lyophilized in the means for localization, immobilization and/or enrichment and/or by opening a blister containing the charged substance without intervention by the user. The means for localization, immobilization and/or enrichment can provide the necessary mixing and incubation of the sample with the means for permeabilization. This can result in permeabilization and/or lysis of compartmentalizing components of the pathogens and/or cells, such as a lipid membrane and/or a cell wall.

As a further step, a labeling ligand, and in particular a fluorescent dye, can be applied to and/or released on at least one antibody, and/or a DNA stain can be applied and/or released, and/or a capture ligand can be applied to and/or released on the means for localization, immobilization and/or enrichment. This can preferably take place without intervention by the user by dissolving a substance lyophilized in the means for localization, immobilization and/or enrichment and/or by opening a blister containing the charged substance. The means for localization, immobilization and/or enrichment can provide the necessary mixing and incubation of the sample with the means for binding and the means for labeling.

It is conceivable to label at least one component of at least one pathogen and/or of at least one cell as a further step. As a result of permeabiling and/or lysing the cell, a means for binding and/or labeling can be ensured access to structures of the pathogens and/or cells, for example within the cells, whereby specific binding, for example of antibodies, to antigens can take place. In the case of fluorescent labeled antibodies, this can generate specific immunostaining.

As a further step, it is conceivable to enrich at least one component of a pathogen and/or a cell, in particular by way of retention and/or magnetic separation in a means for localization, immobilization and/or enrichment. When magnetic nanoparticles are used, for example, as the means for binding, these can bind to structures of the pathogen and/or of the cell, for example by way of a specific antibody, whereby these can be enriched by way of magnetic separation. Alternatively, retention, such as by way of filtration of the sample liquid, can result in the enrichment of components of pathogens and/or cells.

As a further step, imaging-based detection of a pathogen and/or a cell through microscopic magnification and/or image recording, in particular by way of a camera, image processing and/or evaluation in a means for image processing and/or a mobile processor unit may be provided. This includes, in particular, object detection, if necessary, after a fluorescent background has been removed and/or, if necessary, after optical artefacts caused by the design of the test system have been factored out. In the case of immunofluorescence labeling, a fluorescent signal can be recorded in an imaging process by a means for image processing, preferably containing a magnifying unit and a camera, using an illumination unit, so that fluorescent structures of the pathogen and/or cell can become visible in the microscopic image. The means for image processing and/or the mobile processor unit can be used to detect these fluorescent structures, without intervention by the user, and a more in-depth evaluation can be carried out, such as an automatic estimation of the pathogen count per sample volume. The results can also be transmitted to medical treatment specialists by way of the mobile processor unit, which can establish a diagnosis and initiate an appropriate treatment.

It is conceivable to carry out the individual steps individually alone and/or in any arbitrary order.

The test method is preferably used for the detection of diseases. In particular the following diseases are conceivable: infectious diseases, diseases caused by fungi, viruses and/or bacteria, and/or pathogens. Furthermore, in particular the following pathogens are conceivable: adenoviruses, Amylostoma, Ascaris, Babesia, *Bacillus anthracis, Bordetella pertussis, Bordetella parapertussis, Borrelia recurrentis, Brucella* sp., *Campylobacter* sp., cestode, *Chlamydia psittaci, Clostridium botulinum, Corynebacterium diphtheriae, Coxiella burnetii*, human-pathogenic *Cryptosporidium* sp., Ebola virus, *Echinococcus multilocularis, Echinococcus granulosus, Escherichia coli*, enterohemorrhagic strains (EHEC), Eucestoda, *Francisella tularensis*, FSME virus, yellow fever virus, *Giardia lamblia, Haemophilus influenzae*, Hantaviruses, Hepatitis A virus, Hepatitis B virus, Hepatitis C virus, Hepatitis D virus, Hepatitise E virus, influenza viruses, Lassa virus, *Legionella* sp., human-pathogenic *Leptospira* sp., *Listeria monocytogenes*, Marburg virus, measles virus, mumps virus, *Mycobacterium leprae, Mycobacterium tuberculosis/africanum, Mycobacterium bovis, Neisseria meningitidis*, norovirus, poliovirus, *Pseudomonas aeruginosa*, rabies virus, *Rickettsia prowazekii*, rotavirus, Rubella virus, *Salmonella paratyphi, Salmonella typhi, Schistosoma, Shigella* sp., *Taenia saginata, Taenia solium, Trichiuris, Tripanosoma, Tripanosoma brucei, Tripanosoma congolense, Tripanosoma vivax, Trichinella spiralis*, Varizella zoster virus, Vibrio cholerae O 1 and O 139, *Yersinia enterocolitica, Yersinia pestis, Treponema pallidum*, HIV, *Echinococcus* sp., *Plasmodium* sp., *Toxoplasma gondii, Streptococcus pneumoniae* and/or *Streptococcus*, in particular *Plasmodium malaria* pathogens such as *P. falciparum, P. vivax, P. malariae*, in particular in a blood sample.

Preferably, a detection of malaria pathogens is conceivable in the test method, which occur in particular in a blood sample.

Within the scope of the invention, it may likewise be advantageous when the test method can use means for localization, immobilization and/or enrichment for the detection of malaria pathogens in a blood sample. It is possible that at least one structure can be available in infected erythrocytes. The test method can include a means for permeabilization, in particular saponin and/or ammonium chloride, and comprise at least one capture ligand, in particular at least one antibody against plasmodial proteins, which can preferably be coupled to at least one magnetic particle, and in particular a Turbobead, and/or a labeling ligand, preferably at least one fluorescent labeled antibody against plasmodial proteins and/or at least one DNA stain against plasmodial DNA. This can be used to detect at least one structure of plasmodia and/or of the at least one infected erythrocyte in a sandwich structure and/or at least one infected erythrocyte and/or at least one structure of plasmodia can be captured by way of retention and/or magnetic separation in a means for localization, immobilization and/or enrichment.

Moreover, the test method can be configured with a means for localization, immobilization and/or enrichment, which contains at least one microcuvette, also in combination with a microfluidic structure, in which a sample liquid is received, preferably a defined amount of whole blood from the finger pad. In this microcuvette, with or without microfluidic structure, the sample liquid can preferably be mixed with lyophilized substances, such as an anticoagulant and/or a capture ligand, with or without magnetic beads, and/or one or more means for labeling and/or stabilizers and/or a means for lysis and/or permeabilization. The mixing can be intensified, for example, by applying a switchable external magnetic field, by way of which present magnetic particles can be guided through the solution, a fishbone pattern in the channel, vibrations, sound or other mixing methods. Thereafter, the pathogens or pathogen components bound to the means for immobilization, such as magnetic microparticles or nanoparticles, can be immobilized on a vision panel and detected microscopically. Moreover, the test method can contain a means for localization, immobilization and/or enrichment, including at least one microfluidic structure, in combination with a filter structure, such as preferably an absorbent filter pad, such as is present in lateral flow tests, for example.

A sample liquid, such as a defined amount of whole blood from the finger pad, can be placed in the microfluidic structure. The sample liquid can preferably be mixed with lyophilized substances, such as an anticoagulant and/or one or more means for labeling, such as antibodies including fluorescent labeling or gold particles, and/or stabilizers and/or a means for lysis and/or permeabilization. Thereafter, the liquid can be brought in contact with the filter structure, for example by opening a ventilation opening and/or, for example, by displacing and/or by bending the chip and/or by overcoming a flow barrier. The filter structure thereafter absorbs the liquid from the capillary. A capture ligand, such as a specific antibody against pathogen antigens, can be immobilized on the filter structure. Due to the small pore size of the filter structure, such as an absorbent pad, and as a result of taking up the liquid, the pathogens or the components come in contact with the capture ligand and are immobilized. Similarly to a lateral flow test, a band is created; however, the band is not composed of a protein including bound antibodies, as is customary with lateral flow tests, but of labeled pathogens and/or cells and/or the components thereof. Depending on the concentration and labeling method, for example including stain, fluorescent dye, gold particles or beads, this band can be analyzed microscopically and/or photographically and/or visually. At least one of the following can be used, for example, as a possible membrane: BA83, BA85, CF1, CF3, CF4, CF5, CF6, CF7, LF1, MF1, VF2, Fusion 5, GF/DVA, AE, FF120HPFFHP.

According to a further aspect of the invention, a use for diagnosing diseases by way of a test system and/or a test method is conceivable. The use according to the invention entails the same advantages as those that were already described in detail with respect to the test system according to the invention and the test method according to the invention. In particular, a diagnosis at the point of care can even be made by an untrained person, so that the sought pathogens and/or cells can be detected on-site and promptly by way of the test system, instead of using complex laboratory methods.

Further measures improving the invention will be apparent from the following description of several exemplary embodiments of the invention, which are schematically illustrated in the figures. All of the features and/or advantages that are apparent from the claims, the description and/or the drawings, including design details, arrangements in terms of space, and method steps, can be essential to the invention, both alone and in a wide variety of combinations. It should be noted that the figures are only of a descriptive nature and not intended to limit the invention in any way. In the drawings:

BRIEF DESCRIPTION OF THE DRAWINGS

FIG. 1a shows a schematic representation of a target cell prior to permeabilization;

FIG. 1b shows a schematic representation of a target cell after permeabilization;

FIG. 2a shows a schematic representation of a reaction vessel as a means for localization, immobilization and/or enrichment;

FIG. 2b shows a schematic representation of a microchannel as a means for localization, immobilization and/or enrichment;

FIG. 2c shows a schematic representation of a microchannel having a retention device;

FIG. 3 shows a schematic representation of a recorded image and processing after the permeabilization, labeling and capture of pathogens and/or cells; and FIG. 4 shows a schematic representation of a test system.

DETAILED DESCRIPTION OF THE INVENTION

FIG. 1a shows a pathogen and/or an infected cell 10 including specific inner target structures 40, 50, such as an antigen, a protein, a lipid, a glycosaccharide chain, a nucleic acid chain, a peptide or other biomolecules. This may be a pathogen 10 such as a bacterium, which has a compartmentalizing structure 30, for example a cell membrane and/or a cell wall, which essentially partitions the inside of the cell from the outside of the cell. It includes target structures 40, 50 specific to this bacterial species, for example on one or more inner structures 20, such as a thylakoid, ribosome, plasmid, chlorosome, a basal apparatus of a flagellum, a nucleotide, a cytoplasmic side of the cell membrane and/or other components on which target structures, such as antigens, can be found. A capture ligand 60 added to the outer solution and/or dissolved therein, such as a specific antibody, for example including a coupled magnetic nanoparticle 70, such as a Turbobead, and/or a labeling ligand 80, such as a specific antibody having a coupled tag 90, such as a fluorophore, a quantum dot, an enzyme or a gold particle and/or other tag, cannot penetrate into the interior of the bacterium due to the compartmentalizing structure 30, such as a cell wall and/or a lipid membrane and/or another structure.

The cell 10 can likewise be an erythrocyte 10 infected with a malaria pathogen 20 (*Plasmodium* spec.), for example. The target structures 40, 50 can likewise be *Plasmodium*-specific structures, which are arranged inside the erythrocyte.

The erythrocyte is enveloped by a cell membrane, which is a compartmentalizing structure 30 and essentially separates the inside of the cell from the outside of the cell. It includes target structures 40, 50 specific to this bacterial species, for example on one or more inner structures 20, such as plasmodial proteins on the cytoskeleton and/or on an inner membrane. A capture ligand 60 added to the outer solution and/or dissolved therein, such as a specific antibody, for example including a coupled magnetic nanoparticle 70, such as a Turbobead, and/or a labeling ligand 80, such as a specific antibody including a coupled tag, such as a fluorophore, a quantum dot, an enzyme or a gold particle, cannot penetrate into the interior of the erythrocyte due to the compartmentalizing structure 30.

FIG. 1b shows a cell 10 after a means for permeabilization 110, such as saponin, pore inducers, lysing agents, import-triggering agents, hypotonic or hypertonic solutions and/or other substances, has been added. Due to the means for permeabilization, openings 31 in the form of cracks, pores, holes, destabilized membrane areas, for example without cholesterol, and/or a receiving process 31, such as transport mechanisms, can develop in the compartmentalizing structure 30. As a result, the capture ligand(s) 60, including a coupled magnetic nanoparticle 70, and/or the labeling ligand 80, including a coupled tag 90, added to the outer solution can penetrate the cell and/or the pathogen and bind therein specifically to the respective target structure 40 and/or 50. The capture ligand 60 and the labeling ligand 80 preferably have no cross reactivity, which is to say they bind to different target structures 40, 50, whereby preferably a sandwich structure can be created. The binding of the labeling ligand 80, such as a fluorescent labeled antibody, to a target structure 40, such as an antigen typical of a pathogen, can preferably result in immunostaining.

FIG. 2a shows a schematic representation of a reaction vessel 121 as a means for localization, immobilization and/or enrichment containing a sample including cells 10, 11. The cells 10 can preferably represent target cells, and the cells 11 can represent non-target cells. The reaction vessel 121 can be micro reaction vessel, for example, such as an Eppendorf reaction vessel, and/or a chromatography column. An associated magnet 130, such as a high gradient magnet and/or a permanent magnet and/or a solenoid and/or another magnet, can generate a magnetic attractive force 131 in the reaction vessel 121. This attractive force 131 can act on the magnetic nanoparticles 70, whereby these and the target structure 50 bound by way of the capture ligand are attracted and can be enriched and immobilized in spatial proximity to the magnet, to the extent this is possible in the reaction vessel 10. The bound target structure 50 can preferably be joined to components and/or the majority of the cell and/or of the pathogen 10, so that the bound target structure 50 is enriched with attached further components in spatial proximity to the magnet, such as on the wall of the reaction vessel facing the magnet. Non-target cells, such as non-infected erythrocytes, cannot be bound by capture ligands and cannot be enriched. Structures of the target cell can be labeled by way of binding of a labeling ligand, such as a fluorescent labeled antibody and/or a fluorescent labeled DNA stain.

FIG. 2b shows a schematic representation of a microfluidic structure 140 as a means for localization, immobilization and/or enrichment, containing a sample therein, using a capture ligand including a magnetic nanoparticle. A microfluidic structure is composed of a part containing capillaries and/or microstructures and/or one or more microchannels. The sample liquid containing cells 10, 11 therein can flow through the microfluidic structure 140 in the direction of flow 141. An associated magnet 130 can generate a magnetic force 131 in an area of the microfluidic structure. This force can attract the magnetic nanoparticles 70, as shown in FIG. 2a, and thereby act on the coupled capture ligand 60 and a bound target structure 50 and/or preferably a bound majority of the structure 20 and/or 10. This can result in an enrichment of the target structure, and preferably of the cells 10 and/or the components of the microfluidic structure 140, in particular at the top, the side walls and/or the bottom. Cells 11, such as non-infected erythrocytes, cannot be bound by capture ligands 60 and cannot be enriched. A target structure or target structures 40 of the target cell 10 can be labeled by way of binding of a labeling ligand 80, such as a fluorescent labeled antibody and/or a fluorescent labeled DNA stain.

FIG. 2c shows a schematic representation of a microfluidic structure 140 as a means for localization, immobilization and/or enrichment, containing a sample therein, and a retention device in the microfluidic channel. The sample liquid containing cells 10, 11 therein can flow through the microfluidic structure 140 in the direction of flow 141. A retention device in an area of the microfluidic structure can retain cells 10, 11 (target cells and non-target cells) and/or target pathogens 10 contained therein, while the remaining liquid can partially flow in/through the retention device. Furthermore, structures of the cell 10 cell can be labeled by way of binding of a labeling ligand 80, such as a fluorescent labeled antibody and/or a fluorescent labeled DNA stain. Labeled cells 10 (target cells) among the retained cells 10, 11 (target cells and non-target cells) can be detected by way of an image processing device.

FIG. 3 shows the schematic representation of a recorded image and processing after permeabilization, labeling and/or enrichment in the case of fluorescent labeling and imaging-based detection. The sample containing the cells 10 therein can be irradiated with excitation light 151, for example light having a wavelength in the range of 300 nm to 950 nm of an excitation illumination device 150, such as an LED and/or a laser and/or an illumination source. This excitation illumination can be tailored so as to stimulate the tag 90 to emit fluorescent light 152, such as light having a wavelength in the range of 300 nm to 1000 nm. Fluorescent light 152 can thereupon be absorbed by a means for image processing 160. A magnifying unit 161 and a camera 162 can be assigned to this means for image processing 160. Image data of the camera can be processed and transmitted, preferably wirelessly, to a mobile processor unit 163, such as a smart phone, by way of data transmission 164. The mobile processor unit 163 can evaluate this image data and, furthermore, provide user guidance and control the means for image processing. As a result, present cells and/or pathogens can be localized and displayed in the images. A diagnosis can be established by medical treatment specialists, for example, by transmitting the pathogen images to a processor unit 164, such as another mobile smart phone of such specialists.

FIG. 4 shows a schematic representation of a microfluidic structure 200, which contains a capillary and/or a microchannel and/or another microfluidic structure, for example. This may contain a sample receptacle 210, in which a volume of a liquid sample is placed. This may be a capillary having a defined volume, for example. The sample receptacle 210 can contain lyophilized substances, such as an anticoagulant. The sample can then through the microfluidic structure 200, for example based on capillary forces. The sample can be divided therein, for example by way of branching of a microchannel, so that a first portion of the sample can flow through a reservoir for a charged, solid substance 220 and can dissolve lyophilized ligands, for example. In a mixing/incubation chamber, the first sample portion can be mixed with this substance or these substances and incubated. The first sample portion can be combined with a second sample portion and be mixed and incubated in a mixing/incubation chamber 240. Capture, enrichment and/or immobilization can take place in the detection area. The means for image processing can detect the target cells/target pathogens in the detection area. The flow process can preferably be maintained by a suction device 250, such as an absorbent non-woven and/or a micropump, but can also be carried out by an external device, such as a pump. The solution can then be collected in a waste reservoir 260. A microfluidic structure, serving as a test strip, can furthermore include a code, such as a bar code, and/or an RFID component for identifying the sample.

Example of the Detection of Malaria Pathogens

Malaria pathogens undergo several stages during their life cycle. The capillary blood from the finger pad predominantly contains ring-stage plasmodia in infected red blood cells (iRBC). In contrast to the non-infected white blood cells (RBC), the plasmodia contain DNA. A variety of parasitic antigens, such as the PfEMP-1 protein, can be found on the surface of iRBC. For undergoing the immune response, however only one from a pool of many variable, genetically encoded subforms can be found here. So far, no antibodies are known for the pathogen *Plasmodium falciparum* which could universally detect all variants to as great an extent as possible, and thus be used as a universal antibody for the diagnostic identification of all iRBC infected with *Plasmodium falciparum*. However, there are several parasitic antigens inside the iRBC containing ring-stage pathogens which do not variably occur in all Plas. falc. Both polyclonal and monoclonal antibodies against plasmodial proteins are commercially available, such as monoclonal mouse IgM antibodies against *Plasmodium falciparum* of "all stages" and monoclonal anti-MSP-1 and/or MSP-10 antibodies. Another example of a parasitic antigen is the ring-infected erythrocyte surface antigen (RESA), which, in contrast to its name, cannot be found on the surface of the iRBC, but on the inside of the membrane of infected erythrocytes on components of the iRBC cytoskeleton. Additional antigens, which can be detected by way of specific antibodies, can also be found on the parasitophorous vacuole and, after the *Plasmodium* membrane has been permeabilized, also in the cytoplasm of the plasmodia. In one embodiment, a defined volume of preferably 1 to 10 μm whole blood from the finger pad is applied to the test strip. The erythrocytes are permeabilized and/or lysed by a means for permeabilization, preferably saponin and/or ammonium chloride, so that a labeling ligand, preferably a fluorescent labeled antibody, such as the monoclonal mouse IgM antibody against RBC infected with Plas. falc., Clone III66, labeled with DyLight 488 and/or a fluorescent labeled anti-RESA antibody, can diffuse into the iRBC. There, this binds to the infected RBC and creates an immunofluorescent tag. Alternatively, the parasitic DNA can be labeled using a fluorescent DNA stain, such as Hoechst 33342. A filter now retains all the cells and cell components. The fluorescent tag can be rendered visible by way of the magnifying unit comprising the image processing unit, which serves as a fluorescence microscope. In another embodiment, a magnetic nanoparticle is used as the means for binding, such as a Turbobead PEG streptavidin, to which a biotinylated antibody, such as the monoclonal mouse IgM antibodies against RBC infected with Plas. falc., Clone III66, biotinylated, is bound. Following the permeabilization of the RBC and iRBC, the MNP diffuses into the erythrocytes, where it binds specifically to structures of the infected RBC. A fluorescent DNA stain and/or a fluorescent labeled antibody is added as a second means for labeling, which creates immunofluorescence of the iRBC and/or plasmodia. The iRBC are immobilized and enriched in the detection area by way of a magnet and can be detected by way of fluorescence microscopy using imaging. In a further embodiment, nanoparticles, such as the NanoScreenMag particles from Chemicell GmbH and/or the MyQuVigen nanoparticles from Nvigen, Inc., are added as means for binding and labeling to the permeabilized iRBC. These can be immobilized in the detection area by way of a magnet and detected by the optical magnifying unit by way of fluorescence microscopy using imaging. The image data of the fluorescent labeled iRBC can be subjected to a first processing step by the image processing device, such as a background correction and/or compression. In the next step, a search for objects whose intensity can exceed a critical value and/or which can have a certain size and/or pixel count, and are thus defined as pathogens, can be carried out in the images using an object detection app. This evaluation can be carried out in the image processing device and/or in the mobile processor unit. The object detection can be further validated by appropriate controls, such as cell identification under white light illumination and/or fluorescence identification after membrane staining. A diagnosis of the patient can be inferred from the detection of pathogens.

Another possible application example for the detection of malaria pathogens is the addition of saponin as a means for lysis and permeabilization to erythrocytes infected with plasmodia in a whole blood sample. Under the action of saponin, the outer erythrocyte membrane is lysed, and the parasite can be released therefrom, wherein the parasitophorous vacuole is preserved. At least one structure, such as parasitophorous antigens, for example the proteins RAP1 or EXP2, can be found on this parasitophorous vacuole. These are stored in rhoptries, micronemes or dense granules, for example, and are thus already present even in early-stage trophozoites. At least one capture ligand 60 can bind to these, and in particular at least one antibody against plasmodial proteins such as RAP1 or EXP2, for example the monoclonal antibody anti-RAP-1, Clone 2.29, or the monoclonal antibody anti-EXP-2, Clone 2.2. This antibody is preferably bound to at least one magnetic microparticle or nanoparticle 70, and in particular to a Dynabead or Dynabead Myone, and/or at least one or more labeling ligands 80, preferably at least one or more labeled antibodies, such as the monoclonal antibody anti-RAP-1, Clone 2.29, or the monoclonal antibody anti-EXP-2, Clone 2.2, against plasmodial proteins such as RAP1 or EXP2. These antibodies can preferably be labeled with a spectrally distinguishable fluorescent dye, such as DY-396XL from Dyomics GmbH, or quantum dots, such as Qdots from Thermo Fisher Scientific or Candots from Candots GmbH. Moreover, at least one (preferably fluorescent) DNA stain can be used against plasmodial DNA, so as to detect, in particular, at least one structure 40, 50, 20 of plasmodia 20 and/or of erythrocytes 10 infected with at least one or more plasmodia 20, and/or to capture at least one infected erythrocyte 10 and/or at least one structure 40, 50, 20 of plasmodia by way of retention and/or magnetic separation in a means for localization, immobilization and/or enrichment 120, such as a microtiter plate having at least 96, and in particular 1536 wells, a microcuvette, a filter structure without or coated with capture ligands or a fluidic structure.

Example of the Detection of Sepsis Pathogens

Sepsis strikes approximately 18 million patients each year and is fatal in approximately 50% of cases. More than 25 different pathogens can cause sepsis, such as bacteria (meningcocci, streptococci and the like) and/or fungal infections. Commercial rapid tests already exist for streptococci, for example. However, these are usually composed of multiple steps, since first the antigen has to be isolated from the cell wall using multiple reagents and then be detected in an indicator reaction. The high specificity of 95 to 100% is well-documented. However, the sensitivity of the tests is only 70 to 90%, which means that the result is a false negative in 10 to 30%. Infectious bacteria are generally accompanied by a regional and temporal change of the surface antigens. A rapid test according to the invention can be carried out by binding and labeling other antigens, to which ligands would not have access without permeabilization of the cells. Comparable to the detection based on the example of a malaria pathogen, different embodiments exist, such as A) retaining all cells and immunofluorescence detection by way of a fluorescent labeled antibody against an internal, more preserved antigen; B) magnetic capturing and simultaneous fluorescence labeling by way of a fluorescent MNP to which a specific antibody is coupled; and/or C) magnetic capturing by way of an MNP, preferably a Turbobead, using a specific antibody and fluorescent labeling by way of a second fluorescent labeled antibody and/or a DNA stain.

Example of an application of the invention for the analysis of food and/or drinking water: detection of legionella in drinking water Legionella are movable rod-shaped bacteria having an average length of 2 to 5 µm and a diameter of 0.5 to 0.8 µm. They are common in surface water and in drinking water lines in a number of species and serogroups. An infection with Legionella pneumophila occurs through atomized water or mist and can cause what is known as Legionnaires' disease, a severe case of pneumonia that is fatal in 10 to 15% of cases. Commercial rapid tests usually include a sampling device, which is mailed to a laboratory, where it is analyzed by way of a bacteria culture in agar plates within approximately 10 days. One embodiment of the invention can include a test strip, for example, which is designed to filter a volume of drinking water in the range of milliliters to several liters and/or cubic meters, so that all cells, bacteria and pathogens contained therein are retained and situated in the detection area. This can be done, for example, using a microporous filtration membrane having a pore size of 0.45 µm. Afterwards, a means for permeabilizing the pathogens is introduced, for example from a blister contained in the test strip, so that the filtration membrane is incubated therewith. Moreover, for example, a fluorescent labeled antibody and/or fluorescent nanoparticle including an antibody are added, which binds specifically to antigens and/or cellular structures of legionella, to which no access would exist without means for permeabilization and which have a locally and temporally substantially constant structure. The pathogens can be detected by way of immunofluorescence by the magnifying unit comprising the image processing device using imaging. In another embodiment, first a volume of drinking water in the range of milliliters to several liters and/or cubic meters is mixed in a mixing chamber with a means for permeabilization and magnetic microparticles, such as Dynabeads, or nanoparticles, such as Turbobeads, to which a specific antibody against antigens of legionella is coupled. After incubation, the mixture is conducted in a test strip past a magnet in a detection area. The MNPs are captured from the solution, whereby bound legionella and/or the components thereof are immobilized. The fluorescent staining can be carried out using a labeling ligand, such as a fluorescent DNA stain and/or a fluorescent labeled antibody and/or a fluorescent nanoparticle including a bound antibody. The detection can again take place by way of imaging immunofluorescence.

As an extension of this example of an application, a sample, in particular of a body fluid such as urine and/or stool, and/or a food sample and/or a drinking water sample can be used, which can be mixed with a buffer to dissolve the same. Solid components can subsequently be separated, for example by way of filtration, sedimentation and/or centrifugation. Pathogens such as legionella and/or eggs of the pathogens, such as of *Ascaris, Trichiuris*, Amylostoma, *Taenia* worms, can be lysed and/or permeabilized using a means for lysis and/or permeabilization 110. The pathogens, eggs of the pathogens and/or the components thereof can subsequently be labeled using a labeling ligand 80 and/or be enriched by way of a means for localization, immobilization and/or enrichment 120, such as a filter structure and/or magnetic particles, and/or be detected by way of imaging microscopy.

The above description of the embodiments describes the present invention exclusively based on examples. Individual features of the embodiments, provided they are technically expedient, can, of course, be freely combined with each other without departing from the scope of the present invention.

LIST OF REFERENCE NUMERALS

10 target cell or target pathogen
11 cell
20 structure of a cell and/or of a pathogen
30 structure for compartmentalization
31 opening generated in 30 and/or receiving mechanism through 30
40 target structure
50 target structure
60 capture ligand
70 magnetic nanoparticle
80 labeling ligand
90 tag
110 means for permeabilization
120 means for localization, immobilization and/or enrichment
121 reaction vessel
122 retention device
130 magnet
131 magnetic attractive force
140 microfluidic structure
141 direction of flow
150 illumination unit
151 excitation light
152 fluorescent light
160 means for image processing
161 magnifying unit
162 camera
163 mobile processor unit
164 data transmission
165 mobile processor unit
200 microfluidic structure
210 sample receptacle
220 reservoir
230 blister reservoir
240 mixer structure, incubation structure
250 suction device
260 waste reservoir
270 code
280 detection area

The invention claimed is:

1. A test system, the test system comprising at least the following means:
    means for at least permeabilizing or lysing at least one pathogen or at least one cell, the pathogen or cell comprising at least one target structure and having a compartmentalizing structure which essentially partitions the inside of said pathogen or cell from the outside of said pathogen or cell, wherein by the means for at least permeabilizing and lysing comprise a substance for generating a temporary or permanent permeability of said compartmentalizing structure to achieve that capturing and labeling ligands have at least access to at least one target structure;
    means for at least capturing and labeling at least one target structure of said at least one pathogen or cell, the means for at least capturing and labeling comprising at least one labeling ligand for binding to a first target structure of said pathogen or cell and at least one capture ligand for binding to at least a second target structure of said pathogen or cell, wherein the first target structure is different from the second target structure such that the labeling ligand and the capture ligand have no cross reactivity and a sandwich structure composed of at least one capture ligand and at least one labeling ligand can be generated, wherein the labeling ligand comprises a tag, wherein the tag is a fluorophore and wherein the capture ligand comprises a coupled magnetic nanoparticle or microparticle;

means for at least localizing, immobilizing or enriching at least one component at least of a pathogen or of a cell including a microfluidic structure or a reaction vessel for incubating a sample fluid with the at least one labeling ligand and the at least one capture ligand and at least one detection area, wherein a magnet is integrated in the detection area for immobilizing the magnetic nanoparticles or microparticles; and at least a fluorescence spectrometer or an imaging fluorescence microscope for detecting the target structures labeled by the at least one labelling ligand in the detection area, enabling an optical read-out of the detection area.

2. The test system according to claim 1, wherein the means at least for localization, immobilization or enrichment comprises a receiving area for receiving a sample fluid.

3. The test system according to claim 1, wherein at least the means at least for localizing, immobilizing or enriching can at least be used for at least one component of pathogens or cells, wherein at least one component of at least pathogens or cells can be enriched or the means at least for localization, immobilization or enrichment comprises a microfluidic structure at least for dissolving or adding or mixing or incubating substances.

4. The test system according to claim 1, wherein the means at least for localization, immobilization or enrichment comprises at least one microfluidic structure for incubating a sample fluid with at least a capture ligand or a labeling ligand, and at least one detection area, wherein at least one component of at least one labeled pathogen or of at least one labeled cell can be received on the means at least for localization, immobilization or enrichment.

5. The test system according to claim 1, wherein the means at least for localization, immobilization or enrichment comprises at least one microfluidic structure made of polyethylene terephthalate (PET) into which aqueous liquid, can flow, having no further coating.

* * * * *